(12) United States Patent
Gregson et al.

(10) Patent No.: US 11,069,062 B2
(45) Date of Patent: Jul. 20, 2021

(54) AUTOMATED SCREENING OF HISTOPATHOLOGY TISSUE SAMPLES VIA ANALYSIS OF A NORMAL MODEL

(71) Applicant: Deciphex, Dublin (IE)

(72) Inventors: Mark Gregson, Dublin (IE); Donal O'Shea, Dublin (IE)

(73) Assignee: DECIPHEX, Dublin (IE)

( * ) Notice: Subject to any disclaimer, the term of this patent is extended or adjusted under 35 U.S.C. 154(b) by 179 days.

(21) Appl. No.: 16/200,987

(22) Filed: Nov. 27, 2018

(65) Prior Publication Data
US 2019/0164287 A1 May 30, 2019

Related U.S. Application Data

(60) Provisional application No. 62/590,861, filed on Nov. 27, 2017.

(51) Int. Cl.
| | | |
|---|---|---|
| *G06T 7/00* | (2017.01) | |
| *G06K 9/00* | (2006.01) | |
| *G16H 30/40* | (2018.01) | |
| *G16H 50/20* | (2018.01) | |
| *G06K 9/66* | (2006.01) | |

(52) U.S. Cl.
CPC .............. *G06T 7/0014* (2013.01); *G06K 9/66* (2013.01); *G16H 30/40* (2018.01); *G16H 50/20* (2018.01); *G06T 2207/10024* (2013.01); *G06T 2207/20072* (2013.01); *G06T 2207/20081* (2013.01); *G06T 2207/30024* (2013.01)

(58) Field of Classification Search
CPC .......... G16H 50/20; G16H 30/40; G06K 9/66; G06T 2207/10024; G06T 2207/20072; G06T 2207/20081; G06T 2207/30024; G06T 2207/20084; G06T 7/0014
USPC ....................................................... 382/128
See application file for complete search history.

(56) References Cited

U.S. PATENT DOCUMENTS

| | | | | |
|---|---|---|---|---|
| 2016/0058423 | A1* | 3/2016 | Kim et al. | .... G06T 2207/30096 600/407 |
| 2018/0130207 | A1* | 5/2018 | Anderson et al. | .... G06T 7/0014 382/128 |
| 2020/0020098 | A1* | 1/2020 | Odry et al. | ........... G06T 7/0012 382/128 |

FOREIGN PATENT DOCUMENTS

AU 2016201298 A1 9/2017

OTHER PUBLICATIONS

International Preliminary Report on Patentability dated Jun. 2, 2020 for International Application No. PCT/EP2018/082744.
(Continued)

*Primary Examiner* — Siamak Harandi
(74) *Attorney, Agent, or Firm* — Tarolli, Sundheim, Covell & Tummino LLP

(57) ABSTRACT

Systems and methods are provided for screening histopathology tissue samples. An anomaly detection system is trained on a plurality of training images. Each of the plurality of training images represents a tissue sample that is substantially free of abnormalities. A test image, representing a tissue sample, is provided to the anomaly detection system. A deviation from normal score is generated for at least a portion of the test image. The deviation from normal score represents a degree of abnormality in the tissue sample represented by the test image.

20 Claims, 3 Drawing Sheets

(56) References Cited

OTHER PUBLICATIONS

Anonymous: "Isolation Forests for Anomaly Detection Improve Fraud Detection." Oct. 31, 2016, XP055542633 https://blog.easysol.net/using-isolation-forests-anamoly-detection/.

* cited by examiner

AUTOMATED SCREENING OF HISTOPATHOLOGY TISSUE SAMPLES VIA ANALYSIS OF A NORMAL MODEL

RELATED APPLICATIONS

The present application claims priority to U.S. Provisional Patent Application Ser. No. 62/590,861 filed Nov. 27, 2017 entitled AUTOMATED SCREENING OF HISTOPATHOLOGY TISSUE SAMPLES VIA ANALYSIS OF A NORMAL MODEL, the entire contents of which being incorporated herein by reference in its entirety for all purposes.

TECHNICAL FIELD

The present invention relates generally to the field of medical diagnostics, and more particularly to automated screening of histopathology tissue samples via an analysis of a normal model.

BACKGROUND OF THE INVENTION

Histopathology refers to the microscopic examination of tissue in order to study the manifestations of disease. Specifically, in clinical medicine, histopathology refers to the examination of a biopsy or surgical specimen by a pathologist, after the specimen has been processed and histological sections have been placed onto glass slides. The medical diagnosis from this examination is formulated as a pathology report describing any pathological changes in the tissue. Histopathology is used in the diagnosis of a number of disorders, including cancer, drug toxicity, infectious diseases, and infarctions.

SUMMARY OF THE INVENTION

In one implementation, a system is provided for screening histopathology tissue samples. The system includes a processor and a non-transitory computer readable medium storing executable instructions. The instructions include an anomaly detection system trained on a plurality of training images. Each of the plurality of training images represents a tissue sample that is substantially free of abnormalities. An image interface receives the test image and provides the test image to the anomaly detection system. The anomaly detection system generates a deviation from normal score for at least a portion of the test image, representing a degree of abnormality in the tissue sample represented by the test image. A user interface provides the deviation score to a user at an associated output device.

In another implementation, a method is provided for screening histopathology tissue samples. An anomaly detection system is trained on a plurality of training images. Each of the plurality of training images represents a tissue sample that is substantially free of abnormalities. A test image, representing a tissue sample to be tested, is provided to the anomaly detection system. A deviation from normal score for at least a portion of the test image is generated at the anomaly detection system, representing a degree of abnormality in the tissue sample represented by the test image.

In yet another implementation, a system is provided for screening histopathology tissue samples. The system includes a processor and a non-transitory computer readable medium storing executable instructions. The instructions include an isolation forest algorithm trained on a plurality of training images. Each of the plurality of training images representing a tissue sample that is substantially free of abnormalities. An image interface receives the test image and provides the test image to the anomaly detection system. The anomaly detection system generates a deviation from normal score for at least a portion of the test image, representing a degree of abnormality in the tissue sample represented by the test image. A user interface provides the deviation score to a user at an associated output device.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Systems and methods are provided for automated screening of histopathology tissue samples via analysis of a normal model. By a "normal model", it is meant that the model is generated by training an expert system from images that are substantially free of pathologies or other abnormalities. The inventors have determined that a general automate screening process for pathological tissue can be developed by training a model on training images free of abnormalities, and then looking for deviations in test samples from this normal model. As a result, test samples can be prescreened for abnormality in an automated manner, requiring intervention of a pathologist only when an abnormality is found to be present.

Figure 1:
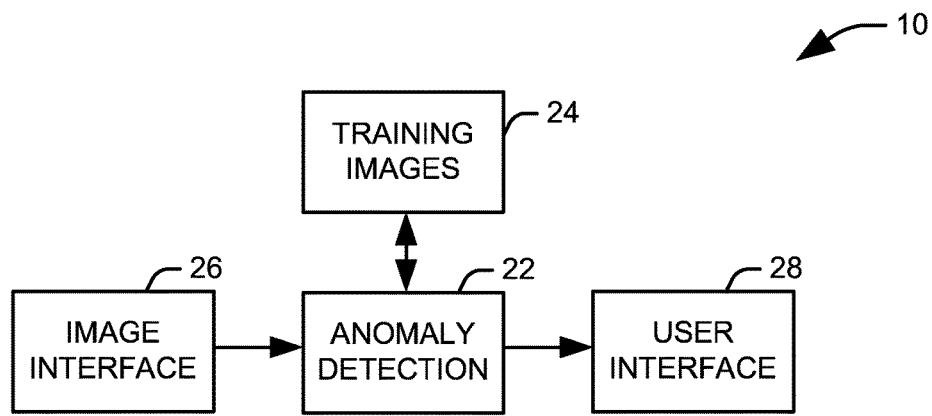
FIG. 1 illustrates a functional block diagram of a system for screening histopathology tissue samples via a normal model.

FIG. 1 illustrates a functional block diagram of a system 10 for screening histopathology tissue samples via a normal model. It will be appreciated that the histopathology tissue samples can include tissue from the gastrointestinal system, the prostate, the skin, the breast, the kidneys, the liver, the lymph nodes, and any other appropriate location in a body of a human or animal subject. Tissue can be extracted via biopsy or acquired via excision or analysis of surgical specimens. In the case of animal subjects, tissue sections can be taken during an autopsy of the animal. The system 10 includes an anomaly detection system 22 trained on a plurality of training images 24. It will be appreciated that the training images 24 can be acquired from stained histopathology tissue samples, for example, hematoxylin and eosin (H&E) stained or immunostained slides, which may have one or more stain normalization processes applied to standardize the images.

In practice, the images can be whole slide images, single frame capture images from a microscope mounted camera, or images taken during endoscopic procedures. The images can be brightfield, greyscale, colorimetric, or fluorescent images, and can be stored in any appropriate image format. Tissue abnormalities can include polyps, tumors, inflammation, infection sites, or other abnormal tissue within a body.

In the liver, abnormalities can include infiltrate, glycogen, necrosis, vacuolation, hyperplasia, hypertrophy, fibrosis, hematopoiesis, granuloma congestion, pigment, arteritis, cholestasis, nodule, hemorrhage, and mitotic figures/regeneration. In the kidney, abnormalities can include infiltrate, necrosis, vacuolation, basophilic tubule, cast renal tubule, hyaline droplet, hyperplasia, fibrosis, hematopoiesis, degeneration/regeneration/mitotic figures, mineralization, dilation, hypoplasia, hypertrophy, pigment, nephropathy, glomerulosclerosis, cysts, congestion, and hemorrhage.

As described above, the anomaly detection system 22 is trained to represent a normal model, and to this end, each of the plurality of training images 24 represents a tissue sample that is substantially free of abnormalities. Accordingly, no images of specific tissue pathologies or other abnormalities is necessary for the training process. In practice, the anomaly detection system 22 can be implemented as any of a plurality of expert systems, along with appropriate logic for extracting classification features from the training images 24 and any submitted test images. In one implementation, the extracted features can include both more traditional image processing features, such as color, texture, and gradients, as well as features derived from the latent space of a variational autoencoder.

Appropriate expert systems can include, for example, density-based techniques, such as k-nearest neighbor, and local outlier factor, subspace-based and correlation-based outlier detection for high-dimensional data, single-class support vector machines, replicator neural networks, cluster analysis-based outlier detection, deviations from association rules and frequent item sets, fuzzy logic based outlier detection, ensemble techniques, isolation forest, one-class random forest, an elliptic envelope approach, for example, utilizing a covariance-weighted distance metric such as the Mahalanobis distance, and a residual image difference from an autoencoder or generative adversarial network. In one implementation, multiple expert systems are utilized, with their individual outputs provided to an arbitrator to provide a deviation from normal score from the plurality of outputs.

An image interface 26 receives a test image, representing a tissue sample for analysis, and provides the test image to the anomaly detection system 22. The anomaly detection system 22 evaluates the test image relative to the model generated from the normal images and generates a deviation from normal score for at least a portion of the test image. The deviation from normal score represents a degree of deviation of the image from the normal model, and thus a degree of abnormality in the tissue sample represented by the test image. In practice, the anomaly detection system 22 can evaluate multiple regions within the image, providing a deviation from normal score for each evaluated region and allowing for localization of abnormalities within the image. A user interface 28 provides the deviation from normal score to a user at an associated output device (not shown), such as a display. In one implementation, the deviation from normal score is calculated for each pixel in the image, and the user interface 28 provides a heatmap representing the tissue sample, in which each pixel is assigned a color associated with a range into which its score falls.

The deviation from normal score can be used for triage, or prescreening, of tissue samples to be analyzed by pathologists, for research, or for diagnosis and monitoring of conditions in a patient. For example, a cohort of tissues can be ranked by overall abnormality scores, allowing pathologists to triage and prioritize patient cases, with the most abnormal cased reviewed first. Alternatively, normal samples can be eliminated and an automatic report of negative findings can be provided, obviating the need for review by a pathologist. Normal samples, as used here, would have an overall abnormality score or focal abnormality score that is less than a set threshold, selected to provide the best performance of the system, based on specificity and sensitivity. The deviation from normal score can also be used to identify and grade abnormalities in the tissue, including quantification and percentage of abnormality, and to evaluate therapeutic responses, predict outcomes, and evaluate biomarkers. In practice, the deviation from normal score can be used to supplement the results of other classifiers applied to detect or identify abnormalities in the tissue. For example, regions of high abnormality can be provided to another classifier for evaluation. Alternatively, multiple classification results, including a global or averaged deviation from normal score, can be used in combination to indicate if an abnormality is present.

Figure 2:
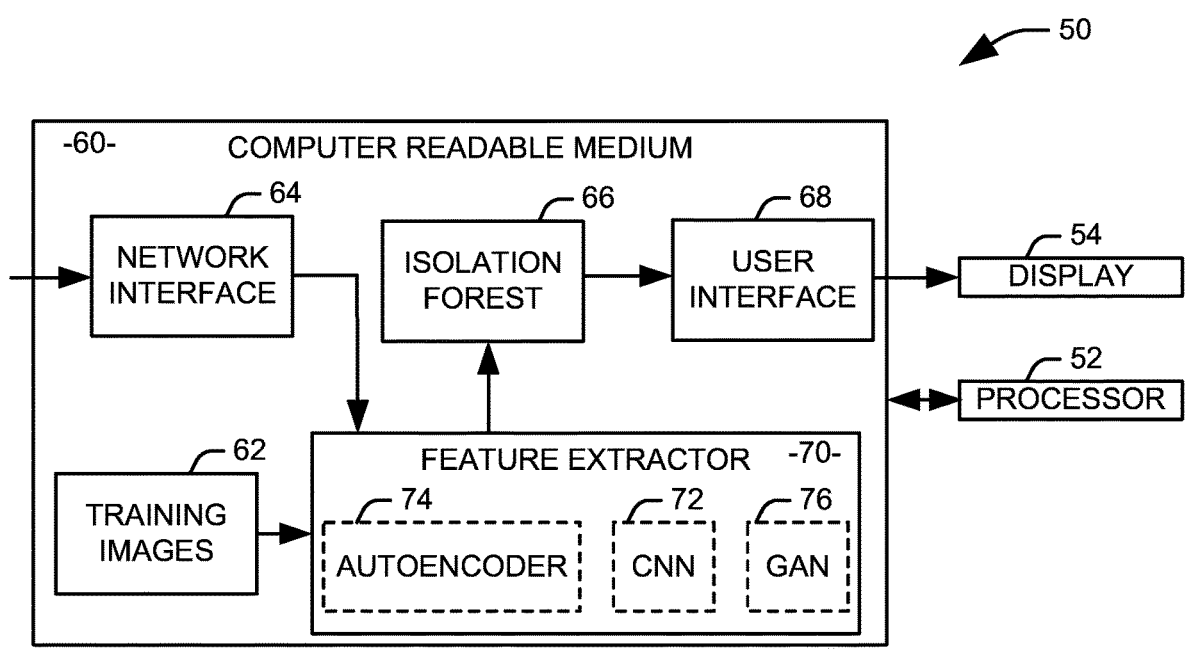
FIG. 2 illustrates an example of a system for screening histopathology tissue samples via a normal model.

FIG. 2 illustrates an example of a system 50 for screening histopathology tissue samples via a normal model. The system 50 includes a processor 52 and a non-transitory computer readable medium 60 that stores executable instructions for evaluating histopathology tissue samples. In the illustrated implementation, the non-transitory computer readable medium 60 stores a set of training images 62, each representing a tissue sample that is substantially free of abnormalities. Each of the set of training images 62 can be provided to a feature extractor 70, which extracts classification features from the training images. It will be appreciated that, instead of storing the training images 62 on the medium 60, they could instead be provided directly to the feature extractor 70 from a remote system via a network interface 64.

The feature extractor 70 can process each image to provide a plurality of feature values for each image. In the illustrated implementation, this can include both global features of the image as well as regional or pixel-level features extracted from the image. In the illustrated implementation, the extracted features can include a first set of features generated from histograms of various image processing metrics for each of a plurality of regions, the metrics including values representing color, texture, and gradients within each region. Specifically, one set of features can be generated from multi-scale histograms of color and texture features. Another set of features can be generated via a dense Speeded-Up Robust Features (SURF) feature detection process.

Additional features can be generated from latent features generated by other expert systems. In the illustrated implementation, the features can include latent vectors generated by a convolutional neural network 72 (CNN), an autoencoder 74, such as a variational autoencoder, and a generative adversarial network (GAN) 76. It will be appreciated that each of the convolutional neural network 72, the autoencoder 74, and the generative adversarial network 76 are trained on the set of training images 62. The convolutional neural network 72, in general terms, is a neural network that has one or more convolutional layers within the hidden layers that learn a linear filter that can extract meaningful structure from an input image. As a result, one or more hidden layers of the convolutional neural network 72 can be utilized as classification features.

The autoencoder 74 is an unsupervised learning algorithm that applies backpropagation to an artificial neural network, with the target values to be equal to the inputs. By restricting the number and size of the hidden layers in the neural network, as well as penalizing neuron activation, the neural network defines a compressed, lower dimensional representation of the image in the form of latent variables, which can be applied as features for anomaly detection. In one implementation, the autoencoder 74 is a variational autoencoder, that works similarly, but restricts the distribution of the latent variables according to variational Bayesian models.

The generative adversarial network 76 uses two neural networks, a first of which generates candidates and the second of which evaluates the candidates. Typically, the generative network learns to map from a latent space to a particular data distribution of interest, taken from a training set, while the discriminative network discriminates between instances from the true data distribution and candidates produced by the generator. The generative network's training objective is to increase the error rate of the discriminative network by producing novel synthesized instances that appear to have come from the true data distribution. As the quality of the synthetic images at the generative network and the discrimination at the discriminative network increase, the features formed in the hidden layers of these networks become increasingly representative of the original data set, making them potentially useful features for defining the normal model.

The extracted features are then provided to an isolation forest algorithm 66 as a feature vector representing the test image. The isolation forest algorithm 66 isolates a given feature vector in feature space by randomly selecting a feature and then randomly selecting a split value between the maximum and minimum values of the selected feature. This is continued until the feature vector is separated from the other feature vectors in the training set or until another termination condition is reached. These separations are represented as isolation trees, or random decision trees, and a score can be calculated as the path length along the tree to isolate the observation. To avoid issues due to the randomness of the tree algorithm, the process is repeated several times, and the average path length is calculated and normalized. It will be appreciated that the isolation forest algorithm 66 is trained on the training set 62 to provide a normal model, and thus the other feature vectors in the isolation forest algorithm represent tissue samples are free from abnormality. Accordingly, test images that differ significantly from normal images should be isolated, on average, fairly quickly, while test images containing abnormalities should be isolated more rapidly. Accordingly, the average path length represents a deviation from normal for the test image, and either the average path length or a function of the average path length can be reported to a user via a user interface 68 as the deviation from normal score at an associated display 54.

Figure 3:
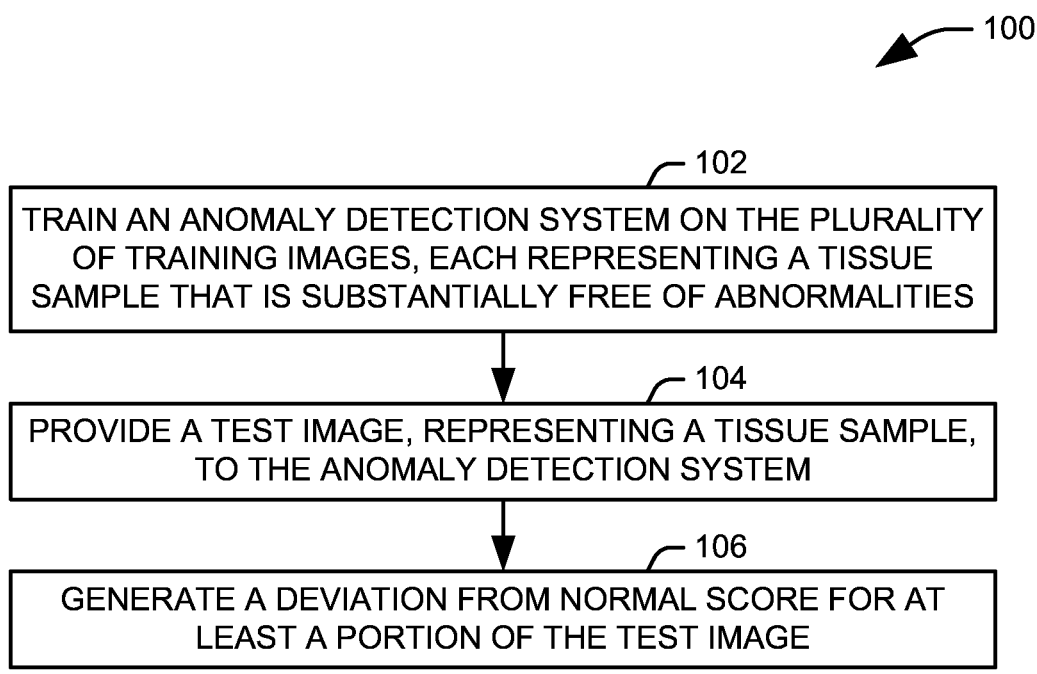
FIG. 3 illustrates one example of a method for screening histopathology tissue samples.
Figure 4:
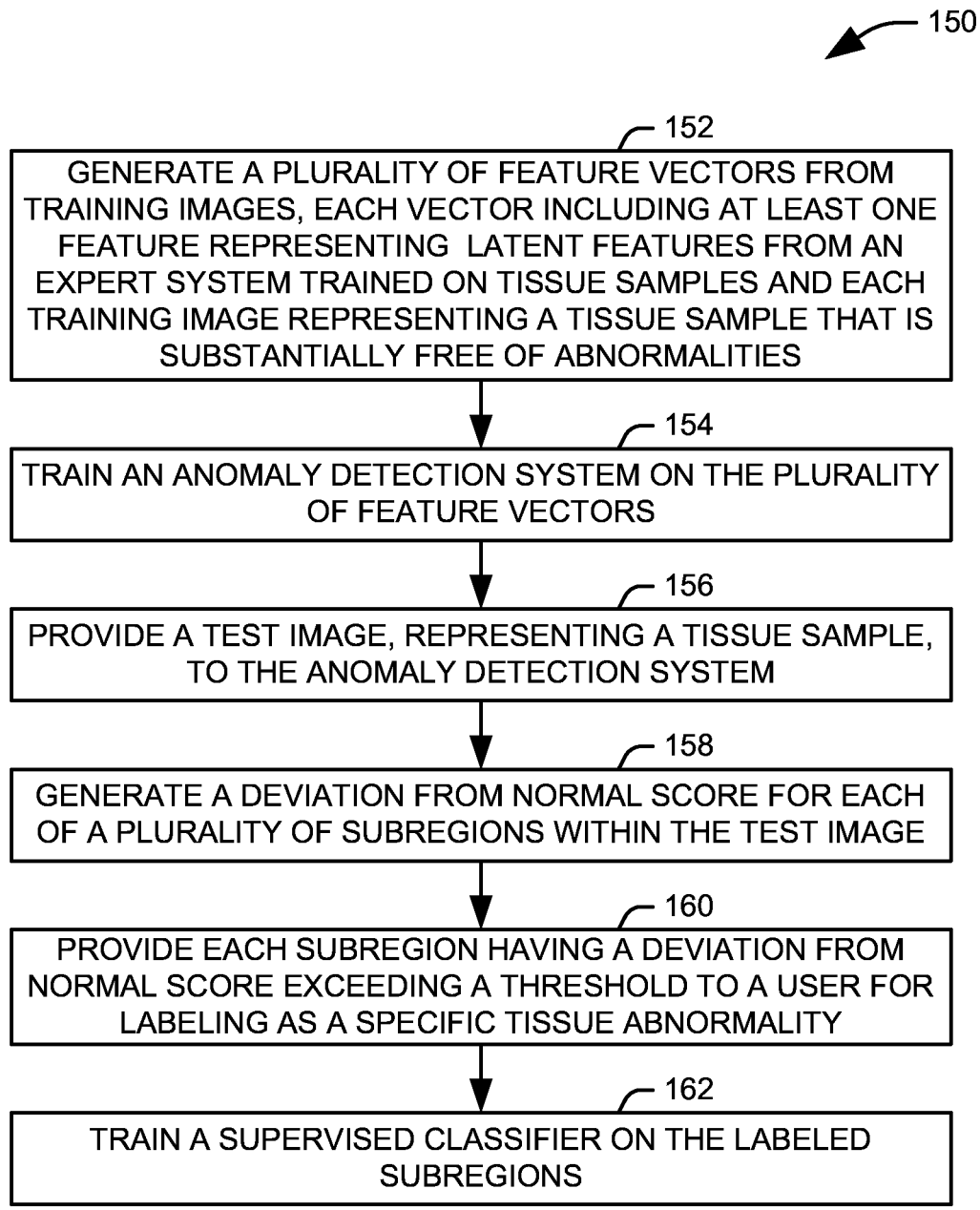
FIG. 4 illustrates one example of a method for generating examples of tissue abnormalities.

In view of the foregoing structural and functional features described above, a method in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 3 illustrates one example of a method 100 for screening histopathology tissue samples. At 102, an anomaly detection system is trained on a plurality of training images. Each of the plurality of training images represents a tissue sample that is substantially free of abnormalities. Accordingly, the anomaly detection system is trained to represent a normal model, in which only tissue samples substantially free of abnormality are represented. At 104, a test image, representing a tissue sample, is provided to the anomaly detection system. In one example, the anomaly detection system can represent the test image as a vector of features, including features derived from color, texture, and gradient values extracted from the image as well as features derived from the latent space of an expert system applied to the image, such as a convolutional neural network, autoencoder, or generative adversarial network.

At 106, a deviation from normal score is generated for at least a portion of the test image using one or more anomaly detection algorithms. The deviation from normal score represents a degree of abnormality in the tissue sample represented by the test image, specifically a degree to which the test image deviates from a normal model represented by the anomaly detection system. In one implementation, the anomaly detection system uses an isolation forest algorithm to generate the deviation from normal score, but it will be appreciated that alternative or additional anomaly detection algorithms can be employed in generating a final deviation from normal score.

In one implementation, the tissue sample is obtained from a patient (e.g., via a biopsy) and used to diagnose or monitor a medical condition in the patient. In another implementation, a therapeutic (e.g., a drug) can be administered to an animal subject for evaluation of the effects of the therapeutic on one or more organs of the subject. In yet another implementation, a therapeutic to a subject associated with the tissue sample after a first set of tissue samples has been evaluated. A second tissue sample can be extracted, analyzed, and compared to the first sample to determine an efficacy of the therapeutic in treating an existing condition.

FIG. 4 illustrates one example of a method 150 for generating examples of tissue abnormalities. At 152, a plurality of feature vectors are created from a plurality of training images. The plurality of feature vectors including at least one feature generated from a latent space of an expert system, and each of the plurality of training images represents a tissue sample that is substantially free of abnormalities. The expert system used to generate the at least one feature can include, for example, an autoencoder, a convolutional neural network, and a generative adversarial network. In one example, a variational autoencoder is utilized. At 154, an anomaly detection system is trained on the plurality of feature vectors. Accordingly, the anomaly detection system is trained to represent a normal model, in which only tissue samples substantially free of abnormality are represented.

At 156, a test image, representing a tissue sample, is provided to the anomaly detection system. The anomaly detection system can represent the test image as a vector of features, including features derived from color, texture, and gradient values extracted from the image as well as the at least one feature derived from the latent space of an expert system. At 158, a deviation from normal score is generated for each of a plurality of subregions of the test image using the anomaly detection system. The deviation from normal score for each subregion represents a degree of abnormality in the tissue sample represented by the subregion, specifically a degree to which that region deviates from a normal model represented by the anomaly detection system. By appropriate selection of the subregion size, the method 150 can not only determine that a test image contains abnormalities, but identify a location and extent of the abnormality with significant precision.

At 160, each subregion having a deviation from normal score above a threshold value is segmented and provided to a user for analysis. Each such subregion represents an abnormality within the tissue, and the user can label each segment with the specific nature of the abnormality. At 162, the labelled subregions can be used to train a supervised classifier system to identify specific abnormalities within the tissue. Accordingly, the method 150 can assist a user to efficiently provide training samples for a supervised classification system from unlabeled test images.

Figure 5:
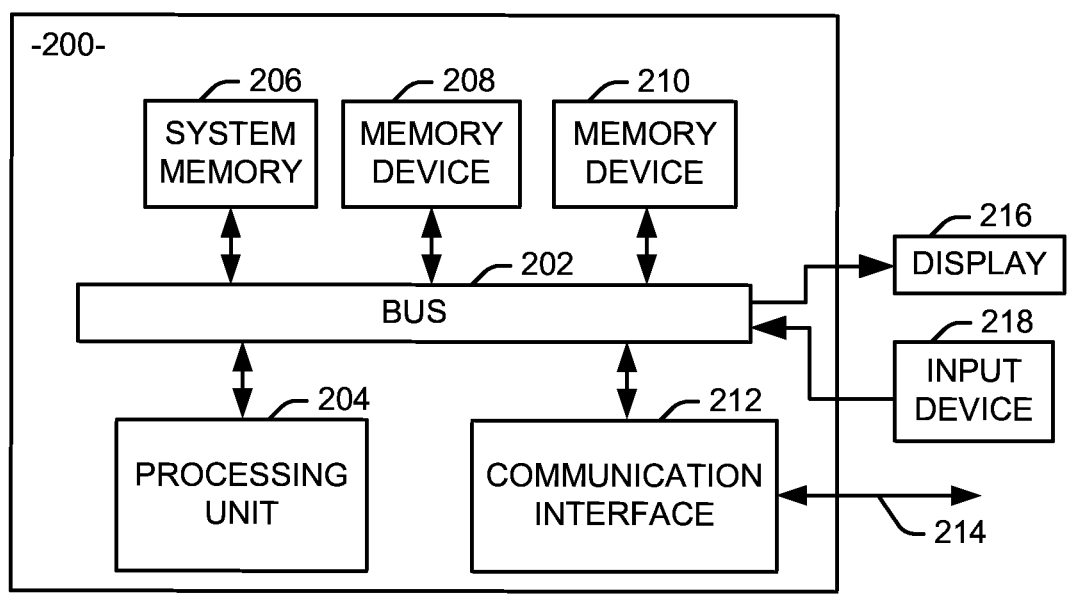
FIG. 5 is a schematic block diagram illustrating an exemplary system of hardware components capable of implementing examples of the systems and methods disclosed herein.

FIG. 5 is a schematic block diagram illustrating an exemplary system 200 of hardware components capable of implementing examples of the systems and methods disclosed in FIGS. 1-4, such as the tissue screening system illustrated in FIGS. 1 and 2. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings. Additionally or alternatively, the system 200 can access an external data source or query source through the communication interface 212, which can communicate with the system bus 202 and the communication link 214.

In operation, the system 200 can be used to implement one or more parts of a tissue screening system in accordance with the present invention. Computer executable logic for implementing the tissue screening system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to any medium that participates in providing instructions to the processing unit 204 for execution, and it will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. In one example, the systems of FIGS. 1 and 2 can be implemented on one or more cloud servers and can be configured to receive feature sets for analysis from one or more client systems.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

From the above description of the invention, those skilled in the art will perceive improvements, changes, and modifications. Such improvements, changes, and modifications within the skill of the art are intended to be covered by the appended claims.

Having described the invention, we claim:

1. A system for screening histopathology tissue samples, comprising:
   a processor; and
   a non-transitory computer readable medium storing executable instructions comprising:
      an anomaly detection system trained on a plurality of training images, each of the plurality of training images representing a tissue sample that is substantially free of abnormalities, the anomaly detection system extracting a plurality of features from each of the plurality of training images that includes a set of features derived from a set of multi-scale histograms of color features;
      an image interface that receives a test image and provides the test image to the anomaly detection system, the anomaly detection system generating a deviation from normal score for at least a portion of the test image, the deviation from normal score representing a degree of abnormality in the tissue sample represented by the test image; and
      a user interface that provides the deviation score to a user at an associated output device.

2. The system of claim 1, wherein the anomaly detection system extracts a plurality of features from each of the plurality of training images, the plurality of features including a set of features derived from a latent space of a variational autoencoder.

3. The system of claim 1, wherein the anomaly detection system comprises an isolation forest algorithm that determines the deviation from normal score as an as average path length along a decision tree to isolate an observation represented by the test image.

4. The system of claim 1, wherein the anomaly detection system comprises a single class support vector machine that generates the deviation from normal score.

5. The system of claim 1, wherein the anomaly detection system comprises a plurality of expert systems that provide respective outputs an arbitrator to provide a deviation from normal score.

6. The system of claim 1, wherein the anomaly detection system extracts a plurality of features from each of the plurality of training images, the plurality of features including a set of features derived from latent vectors generated by a convolutional neural network.

7. The system of claim 1, wherein the anomaly detection system extracts a plurality of features from each of the plurality of training images, the plurality of features including a set of features formed in at least one hidden layer of a generative adversarial network.

8. A method for evaluating the effect of a therapeutic on an organ of a subject from histopathology tissue samples, the method comprising:
   administering the therapeutic to a subject;
   extracting a tissue sample to be tested from the organ of the subject;
   training an anomaly detection system on a plurality of training images, each of the plurality of training images representing a tissue sample that is substantially free of abnormalities;
   providing a test image, representing the tissue sample to be tested, to the anomaly detection system; and
   generating a deviation from normal score for at least a portion of the test image at the anomaly detection system, the deviation from normal score representing a degree of abnormality in the tissue sample represented by the test image.

9. The method of claim 8, further comprising extracting the tissue sample to be tested via a biopsy of a human patient.

10. The method of claim 8, wherein the deviation from normal score is generated for each of a plurality of locations on the test image.

11. The method of claim 10, further comprising comparing the deviation from normal score at each of the plurality of locations to a threshold value to identify a location in the tissue sample represented by the test image containing an abnormality.

12. The method of claim 10, wherein the plurality of locations on the test images are a plurality of pixels comprising the test image.

13. The method of claim 8, wherein generating the deviation from normal score for at least a portion of the test image at the anomaly detection system comprises extracting a plurality of features from the test image, the plurality of features including a set of features derived from one of a latent space of a variational autoencoder, a dense Speeded-Up Robust Features feature detection process, a set of multi-scale histograms of color and texture features, a set of latent vectors generated by a convolutional neural network, and a hidden layer of a generative adversarial network.

14. The method of claim 8, wherein generating the deviation from normal score for at least a portion of the test image at the anomaly detection system comprises providing the extracted plurality of features to one of an isolation forest algorithm and a single class support vector machine.

15. A method for screening histopathology tissue samples, comprising:
   training an anomaly detection system on a plurality of training images, each of the plurality of training images representing a tissue sample that is substantially free of abnormalities;
   providing a first test image, representing a first tissue sample to be tested, to the anomaly detection system;
   generating a first deviation from normal score for at least a portion of the first test image at the anomaly detection system, the first deviation from normal score representing a degree of abnormality in the tissue sample represented by the first test image, administering a therapeutic to a subject associated with the first tissue sample;
   extracting a second tissue sample from the subject;

providing a second test image, representing the second tissue sample to be tested, to the anomaly detection system;

generating a second deviation from normal score for at least a portion of the second test image; and comparing the second deviation from normal score to the second deviation from normal score to the first deviation from normal score to determine an efficacy of the therapeutic.

16. The method of claim 15, wherein the first deviation from normal score is generated for each of a plurality of locations on the test image.

17. The method of claim 16, further comprising comparing the first deviation from normal score at each of the plurality of locations to a threshold value to identify a location in the first tissue sample containing an abnormality.

18. The method of claim 16, wherein the plurality of locations on the first test image are a plurality of pixels comprising the test image.

19. The method of claim 15, wherein generating the first deviation from normal score for at least a portion of the first test image at the anomaly detection system comprises extracting a plurality of features from the first test image, the plurality of features including a set of features derived from one of a latent space of a variational autoencoder, a dense Speeded-Up Robust Features feature detection process, a set of multi-scale histograms of color and texture features, a set of latent vectors generated by a convolutional neural network, and a hidden layer of a generative adversarial network.

20. The method of claim 15, wherein generating the first deviation from normal score for at least a portion of the first test image at the anomaly detection system comprises providing the extracted plurality of features to one of an isolation forest algorithm and a single class support vector machine.

* * * * *